(12) United States Patent
Cremer et al.

(10) Patent No.: US 10,357,293 B2
(45) Date of Patent: Jul. 23, 2019

(54) BONE PLATE WITH ALTERNATING CHAMFERS

(71) Applicant: Stryker European Holdings I, LLC, Kalamazoo, MI (US)

(72) Inventors: Axel Bernhard Cremer, Lommiswil (CH); Jan Heinsohn, Hoboken, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 248 days.

(21) Appl. No.: 15/013,086

(22) Filed: Feb. 2, 2016

(65) Prior Publication Data

US 2017/0215931 A1 Aug. 3, 2017

(51) Int. Cl.
*A61B 17/80* (2006.01)

(52) U.S. Cl.
CPC .......... *A61B 17/8052* (2013.01); *A61B 17/80* (2013.01); *A61B 17/8057* (2013.01)

(58) Field of Classification Search
CPC . A61B 17/8052; A61B 17/80; A61B 17/8057; A61B 17/8061
See application file for complete search history.

(56) References Cited

U.S. PATENT DOCUMENTS

| 4,219,015 | A | * | 8/1980 | Steinemann | A61B 17/80 |
| | | | | | 606/280 |
| 5,601,553 | A | | 2/1997 | Trebing et al. | |
| 6,322,562 | B1 | | 11/2001 | Wolter | |
| 6,786,909 | B1 | * | 9/2004 | Dransfeld | A61B 17/8052 |
| | | | | | 606/280 |
| 7,137,987 | B2 | | 11/2006 | Patterson et al. | |
| 7,776,076 | B2 | | 8/2010 | Grady, Jr. et al. | |
| 8,864,802 | B2 | | 10/2014 | Schwager et al. | |

* cited by examiner

*Primary Examiner* — Olivia C Chang
(74) *Attorney, Agent, or Firm* — Lerner, David, Littenberg, Krumholz & Mentlik, LLP

(57) ABSTRACT

A bone plate has a shaft portion having first and second side surfaces spaced from a centerline of the shaft. A plurality of holes extend from an upwardly facing surface of the shaft to a bone contacting surface. A first hole having a center located closer to the first side of the shaft than the centerline, and a second hole located closer to the second side of the shaft than the centerline. The upwardly facing surface of the shaft having a first tapered area extending from adjacent the first circular hole downwardly towards the second side of the shaft and the upwardly facing surface of the shaft having a second chamfered area extending downwardly from adjacent the second circular hole to the first side of the shaft. The tapered areas having wider and narrower portions with the center of each circular hole located adjacent the wider portion of the tapered area.

14 Claims, 7 Drawing Sheets

BONE PLATE WITH ALTERNATING CHAMFERS

BACKGROUND OF THE INVENTION

The present invention generally relates to an implant such as a bone plate for use in orthopedic surgery, preferably for fixation of bone. The disclosure further relates to an implant system and a method for fracture fixation of bone.

Bone plates may be employed for treating periarticular and/or intra-articular fractures of, for example, the proximal humerus, distal femur, proximal tibia or the distal tibia. Such bone plates are available in a plurality of variations for different applications and can have an I-, T-, L-, cloverleaf- or calcaneal-shape.

Bone plates for periarticular and other fractures can include threaded and unthreaded holes to receive locking and non-locking screws, respectively. The locking screws can be secured to the bone plate, wherein a threaded head of the locking screw mates with a corresponding thread on an inner surface of a plate hole. Further, the non-locking screws (such as compression or cortical screws) are typically inserted through plate holes having an unthreaded curved or conical head portion into bone for providing compression of a fracture by pushing bone fragments towards each other. The configuration of the plate holes is often crucial for the medical success of the implant.

U.S. Pat. No. 5,601,553 relates to an anterior thoracolumbar locking bone plate. The bone plate comprises a plurality of threaded screw holes which are located at both extreme ends of the plate for receiving locking screws. Further, the bone plate is provided with elongated holes with a camming surface for receiving temporary screws. A threaded central hole is arranged at a midpoint of the entire bone plate. The bone plate further comprises a curved lower surface for contacting to bone, and an upper surface having two intersecting planes which meet at a central ridge portion.

U.S. Pat. No. 7,776,076 relates to bone plates having an I-, L- or T-shape. The head portion of the bone plate includes threaded screw holes which are orientated such that the axes of the holes intersect at a point beneath the lower surface of the bone plate. Further, bone screws are threadedly engaged with the holes for rigidly anchoring the bone plate to the fractured bone.

U.S. Pat. No. 7,137,987 relates to a bone plating system for fixating distal or proximal ends of long bones. The bone plate has a T- or fork-shaped head portion. The head portion of the bone plate includes a plurality of threaded plate holes for receiving locking bone screws. Further, one or more non-threaded plate holes for receiving a non-locking cancellous bone screw are provided near the peripheral side of the head portion.

U.S. Pat. No. 8,864,802 relates to a bone plate having a curved shaft and a plurality of screw receiving holes spaced on opposite sides of a centerline of the shaft. The disclosure of U.S. Pat. No. 8,864,802 is incorporated herein by reference.

BRIEF SUMMARY OF THE INVENTION

Aspects of the present disclosure are directed to facilitating a rapid healing of a bone fracture and guaranteeing a high screw-plate-bone construct stability.

According to a first aspect, there is provided an implant comprising a shaft region having one or more holes for receiving bone fasteners, and a head region extending from the shaft region and having a plurality of circular holes for receiving bone fasteners. Bone fasteners can, for example, include locking screws, non-locking screws such as compression or cortical screws, and bone pegs having rod-like or pin-like shafts.

Each locking screw hole may include (e.g., a hole portion with) a locking structure adapted to lock a bone fastener to the implant. The locking structure can include a threaded portion or a circumferential lip adapted to lockingly engage a bone fastener. Alternatively, the locking structure may have one or more protrusions extending in a radial direction of the locking screw hole. A bone fastener can be polyaxially or monoaxially insertable through the locking screw hole, such that the locking structure may receive a head portion of a bone fastener for locking engagement therebetween. Alternatively, a bone fastener having a self-cutting portion can be inserted into the locking screw hole for engaging the locking structure. The locking structure of each locking screw hole can be realized in the form of any of the hole configurations described in U.S. Pat. No. 6,322,562.

The shaft region of the implant may be shaped to conform to an extra-articular part of a bone and the head region of the implant may be shaped to conform to a periarticular part of the bone. The length of the shaft may be curved. The head region may generally be round (e.g., oval or circular). As an example, the implant may generally have a spoon-like shape (with a generally round or oval head) or a L-like shape (with a generally linear head).

A transition from the shaft region to the head region may be defined by an increasing width in an axial direction of the implant. Further, a (e.g., maximal) width of a portion of the head region facing the shaft region may be greater than a (e.g., maximal) width of the shaft region. Thus, the head region may start when a width of the implant continuously enlarges in the distal direction of the implant.

The head region can have a length approximately between 10 mm and 100 mm and a width approximately between 10 mm and 50 mm. Alternatively, the head region may have a width varying over the entire length thereof. Moreover, the width of the head region may be greater than a width of the shaft region. The head region may have an I-, T-, L-, cloverleaf- or calcaneal-shape.

The shaft portion of the implant has a plurality of circular screw holes and may further include at least an oblong hole (e.g., at an end facing the head). Moreover, the oblong hole may include a cylindrical hole portion on a bone contacting side of the implant and a curved or conical hole portion on a side opposite to the bone contacting side. The oblong hole can have a length approximately between 5 mm and 10 mm and a width approximately between 2 mm and 8 mm. The oblong hole may have a region of tapering width between a region of maximum width and a region of minimum width. The oblong hole may also be at least partially threaded. Multiple oblong holes can be provided along the shaft length.

The head region may include at least one K-wire (Kirschner wire) hole for receiving a K-wire, wherein a diameter of the K-wire hole is smaller than a diameter of each of the central screw hole and the surrounding screw holes. The diameter of the K-wire hole may be approximately between 1 mm and 3 mm. The K-wire hole can further include a threaded hole portion. In one implementation, the head region may include at least one targeting structure (comprising, e.g., a targeting hole) for receiving a targeting instrument. The targeting structure may include grooves on an implant surface. The grooves can substantially extend in the radial direction of a targeting hole.

At least one hole of the implant may have a central axis which is oblique relative a vertical axis of the implant. An angle defined between the central axis and the vertical axis can be approximately between 0° and 60°. Alternatively, the at least one hole may be oblique relative to an upper surface or lower surface of the implant.

An outer peripheral surface of the shaft region may have an undulating or collapsed shape, such that the shaft region can have a series of waisted shapes. Further, the shaft region may have a length approximately between 40 mm and 400 mm and a width approximately between 5 mm and 20 mm. Alternatively, the width can vary over the entire length of the shaft region. The shaft region can further have a curved shape (e.g., C-shape) in a longitudinal direction thereof.

The locking screw holes may be adapted to receive cortical screws for fixing the implant to bone. The implant can be configured as a bone plate. The implant may have a length approximately between 50 mm and 500 mm and a width approximately between 5 mm and 50 mm. Alternatively, the width can vary over the entire length of the implant. Moreover, the implant can have a thickness approximately between 1 mm and 6 mm. Alternatively, the thickness can vary over the entire length of the implant.

According to a further aspect, there is provided an implant system comprising an implant with a shaft region having one or more holes for receiving bone fasteners, and a head region extending from the shaft region and having a plurality of circular holes for receiving bone fasteners. The plurality of circular holes includes a central (threaded or unthreaded) screw hole having a center and at least three locking screw holes each having a center and surrounding the central screw hole, wherein the centers of the locking screw holes define a polygon and wherein the center of the central screw hole is located on or within the polygon. The implant system further comprises a compression screw adapted to be inserted into the central screw hole, and at least three locking screws or cortical screws adapted for locking engagement with the locking screw holes.

Each locking screw hole of the implant may include a hole portion with a locking structure adapted to lock a bone fastener to the implant. The locking structure may be configured as generally described above.

The implant may further comprise an oblong hole for receiving a further compression or locking screw.

The head region of the implant may include at least one targeting structure for receiving a targeting instrument. The targeting structure can include a targeting hole.

According to a further aspect, there is provided a system comprising an implant with a shaft region having one or more holes for receiving bone fasteners, and a head region extending from the shaft region and having a plurality of circular holes for receiving bone fasteners. The plurality of circular holes includes a central (threaded or unthreaded) screw hole having a center and at least three (threaded or unthreaded) locking screw holes each having a center and surrounding the central screw hole, wherein the centers of the locking screw holes define a polygon and wherein the center of the central screw hole is located on or within the polygon.

The system may further comprise a targeting instrument adapted to be secured to the implant.

The head region of the implant may further include at least one targeting structure comprising, e.g., a targeting hole for receiving the targeting instrument. A portion of the targeting instrument can be adapted to be fixedly secured to the targeting structure of the implant. Further, the targeting instrument may include a plurality of guide holes for guiding bone fasteners, drilling instruments or guiding instruments.

According to a further aspect, there is provide a method for fracture fixation of bone comprising the steps of fixing an implant against bone with at least one bone fastener, wherein the implant comprises a shaft region having one or more holes for receiving bone fasteners, and a head region extending from the shaft region and having a plurality of circular holes for receiving bone fasteners, the plurality of circular holes including a central (threaded or unthreaded) screw hole having a center and at least three locking screw holes each having a center and surrounding the central screw hole, wherein the centers of the locking screw holes define a polygon and wherein the center of the central screw hole is located on or within the polygon; inserting a compression screw through the central screw hole of the implant into bone for compressing the fracture of bone; and inserting at least three locking screws or cortical screws into the locking screw holes of the implant for producing a locking engagement therebetween, thereby stabilizing the truss formed by the implant, the screws and bone.

The present invention relates to a bone plate implant with a head portion and a shaft portion wherein the shaft portion has holes to hole bone screws alternating above and below a centerline of the shaft portion in combination with related scalloped/chamfered areas. A screw hole below the centerline is combined with an enlarged scalloped/chamfered area above the centerline and vice versa. This invention allows for a shaft design with better/increased chamfers and less material within the body that can decrease soft tissue irritation. This shaft design also decreases bending stiffness which can benefit bone healing. Such a bone plate has a shaft having a bone contacting surface and an opposite outwardly facing surface. The shaft has first and second side surfaces spaced from a centerline of the shaft. The first and second side surfaces defining a width of the shaft.

A plurality of holes extend from the outwardly facing surface to the bone contacting surface spaced along the shaft. Each of the holes defines a diameter located intermediate the width of the shaft. A first hole of the plurality of holes having a center of a circular diameter located closer to the first side of the shaft than the centerline, and a neighboring second hole having a center located closer to the second side of the shaft than the centerline.

The outwardly facing surface of the shaft has a first chamfered area extending from adjacent the first hole towards the second side of the shaft and the upwardly facing surface of the shaft having a second chamfered area extending from adjacent the second hole to the first side of the shaft. The chamfered area includes a tapered surface tapering towards the bone contacting surface from the outwardly facing surface. The tapered surface having wider and narrower portions with the center of each hole preferably located adjacent the wider portion of the tapered surface.

Preferably the shaft has at least three circular holes with the first and third holes closer to the first side of the plate shaft and the second hole closer to the second side of the plate shaft. The second hole located intermediate the first and third holes.

In one embodiment the shaft centerline is curved in a direction perpendicular to the longitudinal axis of the plate, although it could be straight. The shaft first and second side surfaces are scalloped with portions extending toward and away from the centerline along a length of the bone plate shaft. In addition, the bone contacting surface between the first and second side surfaces may be concave. It is also possible to have this surface be planar.

Preferably the closest approach of the chamfer tapered surface to the shaft centerline is at the center of each hole. A portion of an upper-most surface of the tapered surface closest to the bone contacting surface is spaced from the bone contacting surface by a portion of the first or second side surfaces. Thus the angle of the chamfered area from the hole to the plate edge is such that a sharp edge is avoided.

The bone plate shaft has a free end, wherein the first and second side surfaces converge to form a tip at the free end with a width tapering inwardly from each side towards the centerline. The tip has a rounded end and with a third hole adjacent the tip, the third hole offset from the centerline towards the first wall, the first and second side surfaces tapering outwardly from the uppermost surface around the third hole to adjacent the bone contacting surface around a circumference of the tip rounded end. The taper angle of the second side surface from the upper-most surface around the third hole to the bone contacting surface being less than the taper angle from the upper-most surface to the bone contacting surface of the first side surface.

The bone plate shaft may include five circular holes with three holes located closer to the first side of the bone plate shaft from the centerline and two holes located closer to the second side of the bone plate shaft from the centerline. One of the two second holes separates the three first holes from each other with one of the at least three holes located closer to the shaft end with each of the three holes including the chamfered tapered surfaces.

In one embodiment, the shaft first and second side surfaces are scalloped with portions extending toward and away from the centerline along a length of the bone plate shaft. This results in the plate shaft having a varying width.

The bone plate of the present invention has a head portion connected to a shaft portion, the head portion and the shaft portion having a bone contacting surface and an opposite outwardly facing surface. The shaft has first and second side surfaces spaced from a centerline of the shaft, the first and second side surfaces defining a width of the shaft. The bone plate has at least three holes extending from the outwardly facing surface to the bone contacting surface spaced along the shaft portion. Each of the holes defining a diameter located intermediate the width of the shaft. A first and third hole of the at least three holes having a center of the diameter located closer to the first side of the shaft than the centerline of the shaft. A second hole of the at least three holes having a center located closer to the second side of the shaft than the centerline.

The outwardly facing surface of the shaft having a first chamfered area extending from adjacent the first hole towards the second side of the shaft and the upwardly facing surface of the shaft having a second chamfered area extending from adjacent the second hole to the first side of the shaft. The chamfered area comprising a tapered surface tapering towards the bone contacting surface from the outwardly facing surface. The tapered surface having wider and narrower portions measured from the centerline on moving longitudinally, with the center of each hole located in the wider portion of the tapered surface. The first and third holes are closer to the first side of the plate and the second hole is closer to the second side of the plate. The second hole is located intermediate the first and third holes.

DESCRIPTION OF THE DRAWINGS

Figure 1:
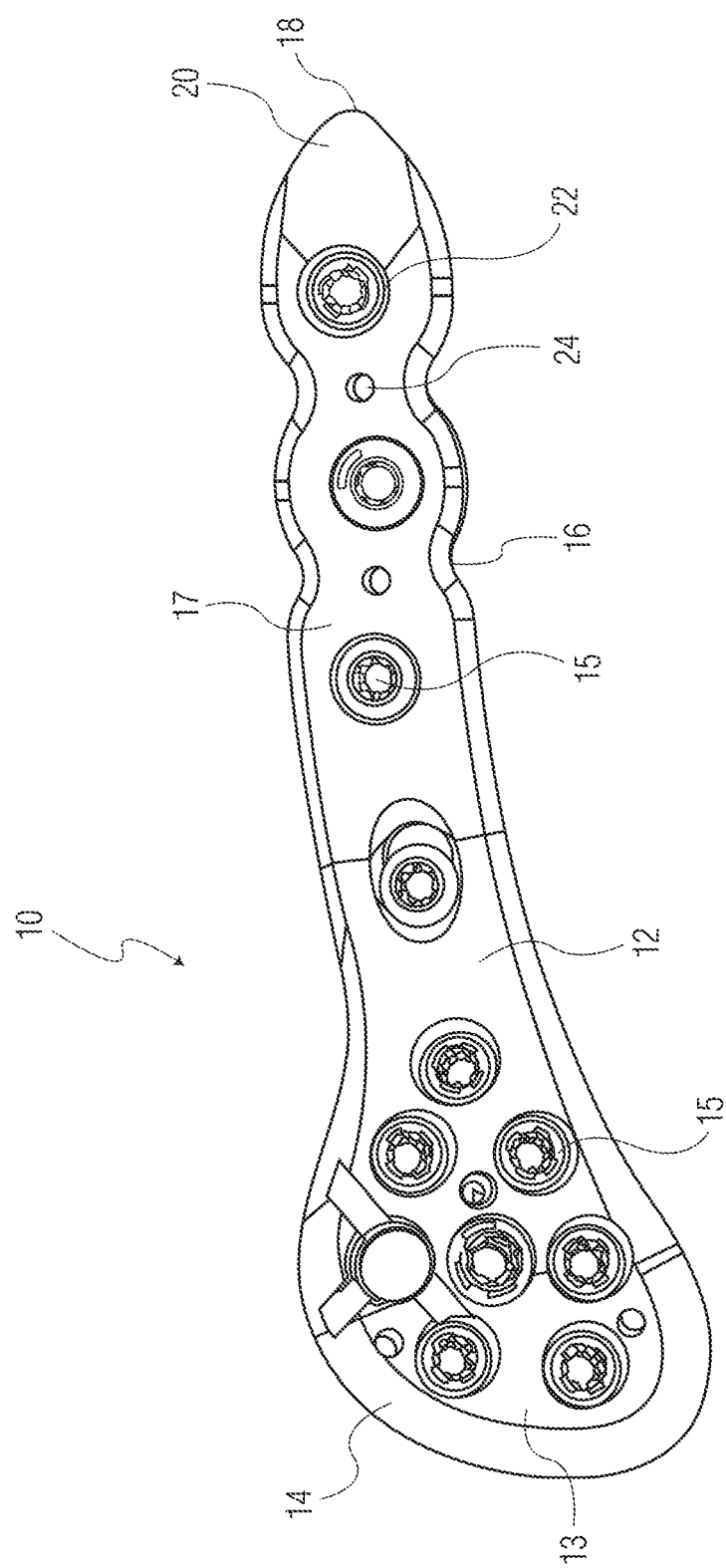
FIGS. 1 and 1A show prior art bone plates having an enlarged head region and a narrowing shaft region.
Figure 1A:
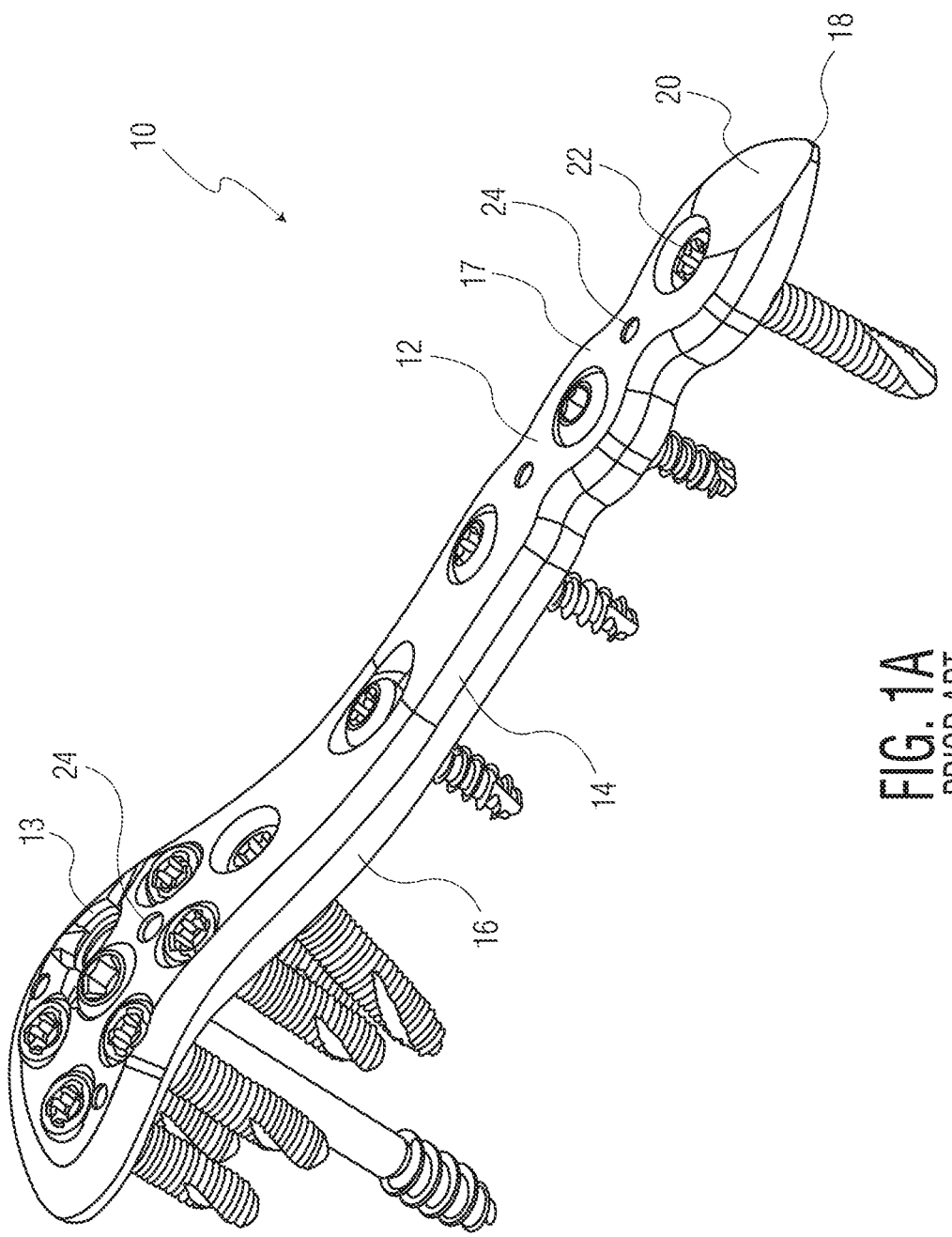

Referring to FIGS. 1 and 1A there is shown a prior art bone plate such as disclosed in U.S. Pat. No. 8,864,802, the disclosure of which is incorporated herein by reference, generally denoted as 10. Bone plate 10 has an upwardly facing surface 12, a plurality of through holes 15 for receiving bone screws, a chamfered surface 14 tapering to a bone contacting surface and an outer edge surface 16 extending around the perfiery of the bone plate. Guide pin holes 24 are usually provided. Surface 14 tapers downwardly from upwardly facing surface 12 to edge 16. The chamfer 14 is essentially uniform around a head portion 13 and shaft portion 17 of bone plate 10 with the exception of the tip 18 which has a tapered surface portion 20 extending from a distal-most bone screw hole 22 to tip 18. Chamfered surface 14 of bone plate 10 is typically spaced from the bone contacting surface by a vertical edge surface 16. The slope of surface 20 is typically about 15°. A more complete description of the prior bone plate 10 may be found in connection with the description of FIGS. 4 and 6 of the aforementioned patent.

Figure 2:
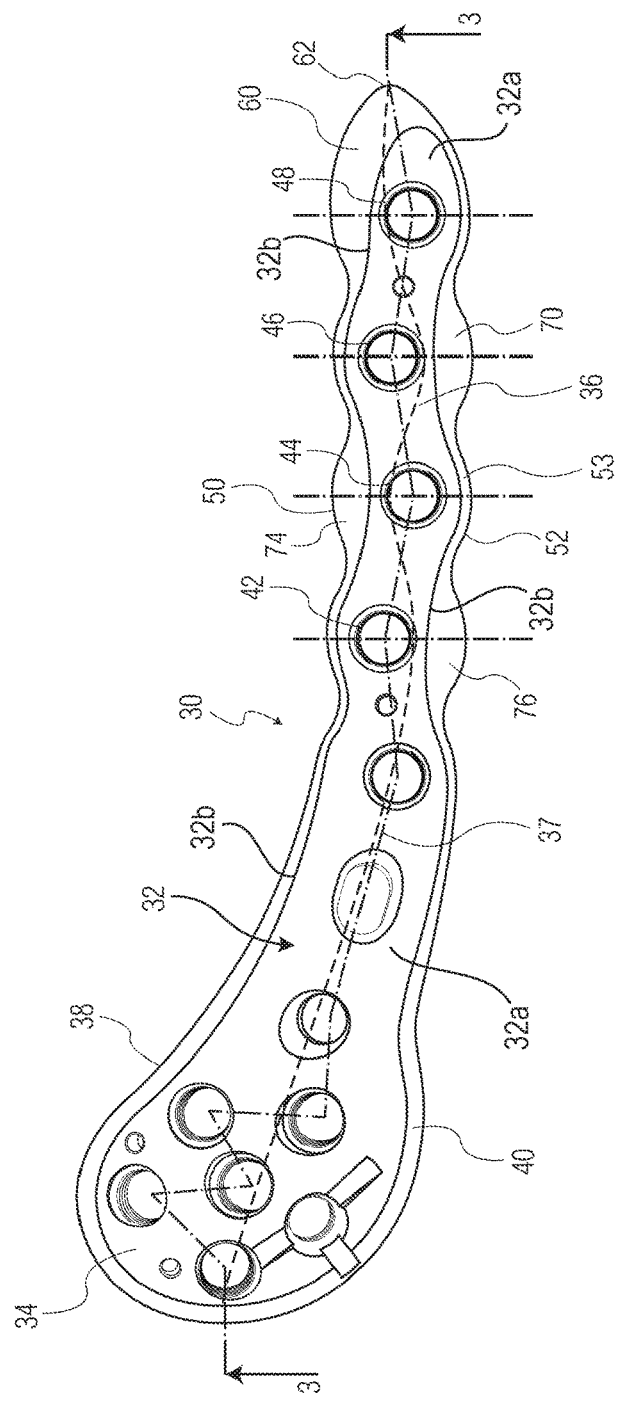
FIG. 2 shows a top view of the bone plate of the present invention having a curved shaft portion with screw holes offset from the centerline of the shaft portion.

Referring to FIG. 2, there is shown the bone plate of the present invention generally denoted as 30 having an upper surface 32 which faces away from the bone when bone plate 30 is mounted on a bone (not shown). The upper surface 32 has top surface segment 32a completely delineated by an edge 32b. Bone plate 30 has many of the features of the prior art plates and includes a head portion 34 and a shaft portion 36 with the shaft and head portions 34, 36 extending along a centerline 39 of plate 10 which may either be straight or arcuate. In head area 34, the upper surface 32 tapers downwardly beyond the edge 32a towards an edge surface 38 to define a chamfered area 40 which chamfer head area 40, has a generally uniform width and slope angle extending from surface 32 to edge surface 38.

The shaft portion 36 includes, for example, four holes, 42, 44, 46, and 48 designed to receive either locking or non-locking bone screws when the bone plate is mounted on bone. The number of holes can vary from three to a maximum of any number depending on the length of shaft portion 36. As can be seen in FIG. 2, holes 42 and 46 are spaced from the centerline 39 of the shaft portion 36 closer to a first side of the bone plate 50, whereas holes 44 and 48 are spaced from the centerline of the shaft portion 36 closer to a second side 52. This offset between adjacent holes allows for the utilization of a wider chamfered area 76 on the second side 52 of plate 30 in the area of hole 42. Likewise, with respect to holes 44, 46, and 48, enlarged chamfered areas 60, 70 and 74 are provided adjacent one of sides 50, 52 of the bone plate spaced further from the centers of the respective holes than the small chamfered areas, for example at 53, on the opposite sides of the bone plate. This results in alternating offset holes along the shaft portion 36 and alternating enlarged chamfered area.

Figure 3:
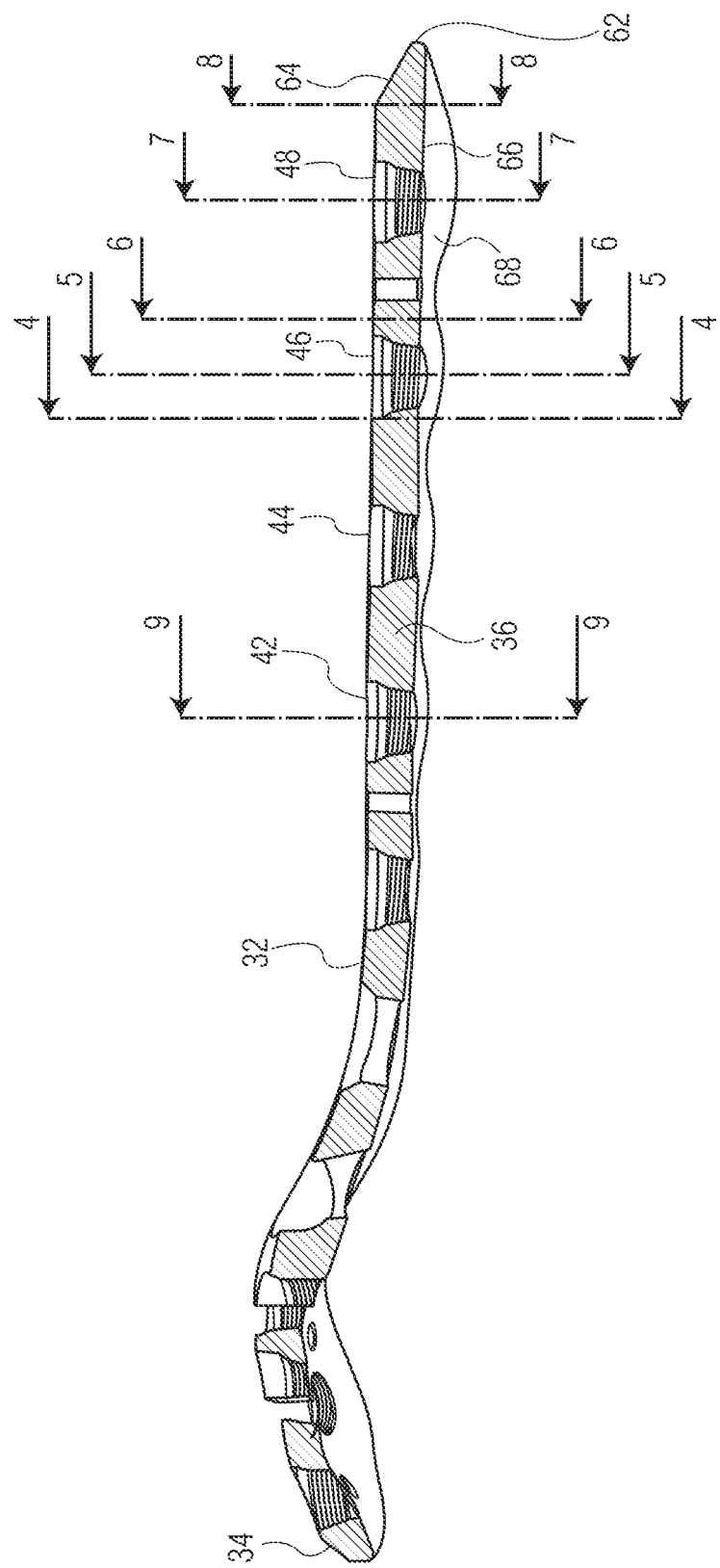
FIG. 3 shows a cross-section of the bone plate of FIG. 2 along lines 3-3 of FIG. 2.

Referring to FIG. 3, there is shown a cross-section of the bone plate of FIG. 2 along lines 3-3. As can been seen in FIG. 3, shaft portion 36 has a free-end with a tip 62 including a chamfered surface 64 extending from tip 62 upwardly towards the distal-most hole 48. Also shown is a bone contacting surface 66 which is opposite from the upwardly facing surface 32. Plate edge surface 38 extends in a direction generally perpendicularly to surface 32 from surface 66. In the preferred embodiment, bone contacting surface 66 may be arcuate as shown at 68 as well as in FIGS. 4 through 9, in order to better conform to the shaft of a long bone. Also as shown in FIG. 3, the head portion 34 can be angled away from shaft portion 36 in a direction perpendicular to the centerline to better conform to the enlarged area at the end of a long bone.

Figure 4:
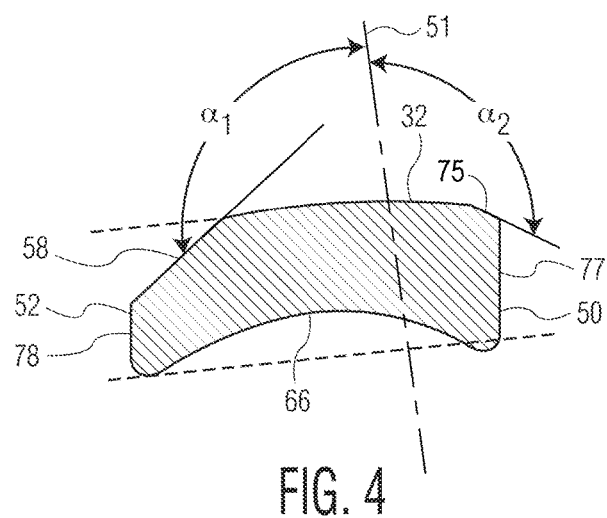
FIGS. 4-9 show cross-sectional views of the bone plates of FIGS. 2 and 3 along lines 4-4 through 9-9 of FIG. 3.

Referring to FIG. 4, there is shown a cross-section through lines 4-4 of FIG. 3, which is tangent to hole 46 at a point closest to the head area 34 of bone plate 30. As can been seen from FIG. 3, the view in FIG. 4 along lines 4-4 show an angled line 58 which is part of an enlarged chamfered area 70 around hole 46 in FIG. 2 tapered toward side 52 of shaft portion 36. Line 58 is angled at angle α1, which is about 125° from line 51. Upper surface 32 and bottom bone contacting surface 66 are connected by edge 38 and chamfered area 58 on side surface 52. On the other plate side 50, it can be seen that the length of line 78 on side 52 is significantly less than the length of line 77 on side 50 as a result of tapered shorter surface 75. Tapered surface 75 is angled at an angle α2 with respect to line 51.

Figure 5:
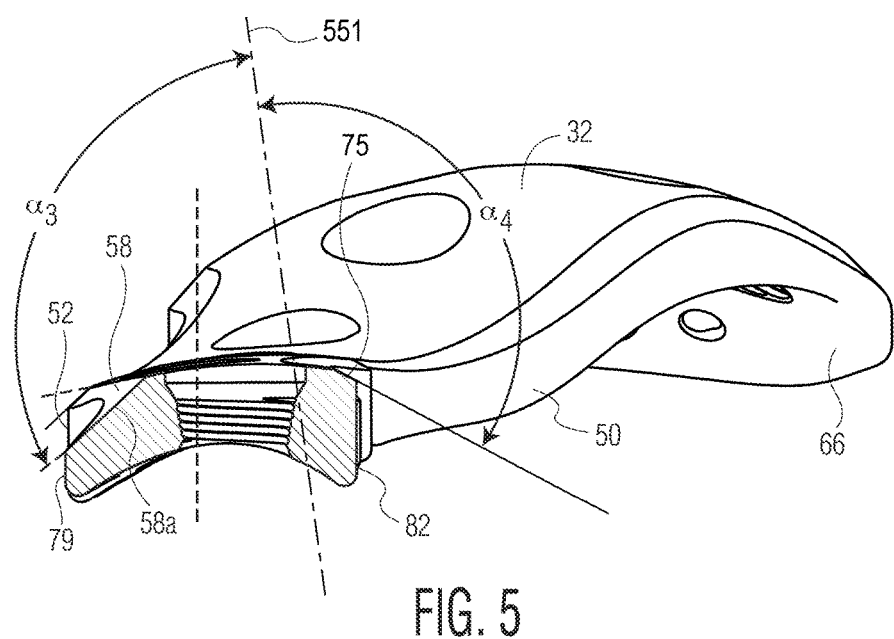

Referring to FIG. 5, there is a cross-sectional view along lines 5-5 of FIG. 3, which cross-section extends through the centerline of hole 46, and line 58a which has the steeper taper angle α3 extending from top surface 32 towards bottom surface 66 to produce chamfered tapered surface 70 of FIG. 2. On side 52 surface 58a extends at angle α3 which is greater than the angle α of a tapered surface 75 adjacent side 50 with respect to surface 32. Thus the height of the plate edge 38 represented by line 79 on side 52 thereof is less than the length of line 82 on side 50 of the plate 30. α3 and α4 are about 125° measured from line 551.

Figure 6:
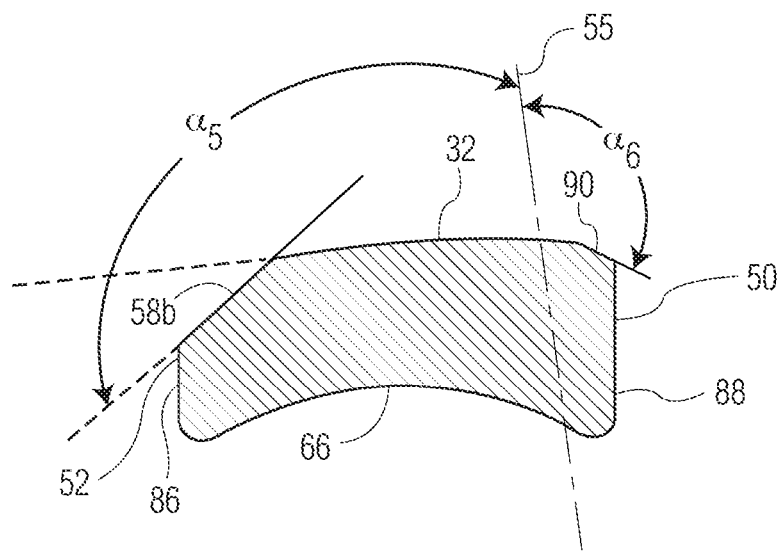

Referring to FIG. 6, there is shown a cross-section just distal (towards the tip 62) from hole 46, which again shows part of chamfered or tapered area 70 of FIG. 2 connecting a now somewhat longer line segment 86 of edge 38 which extends from bone contacting surface 66 to the angled line 58b on side 52 of the cross-section of FIG. 6. Line segment 86 is less than the side thickness represented by line 88 along side 50 of the plate which connects to upper surface 36 via a small chamfer 90. The length of line 58a is longer than lines 58 and 58b since it is as the center of hole 46. The tapered line 58b is angled at α5 with respect to line 55 and with line 90 angled at α6. Both angles are about 125°.

Figure 7:
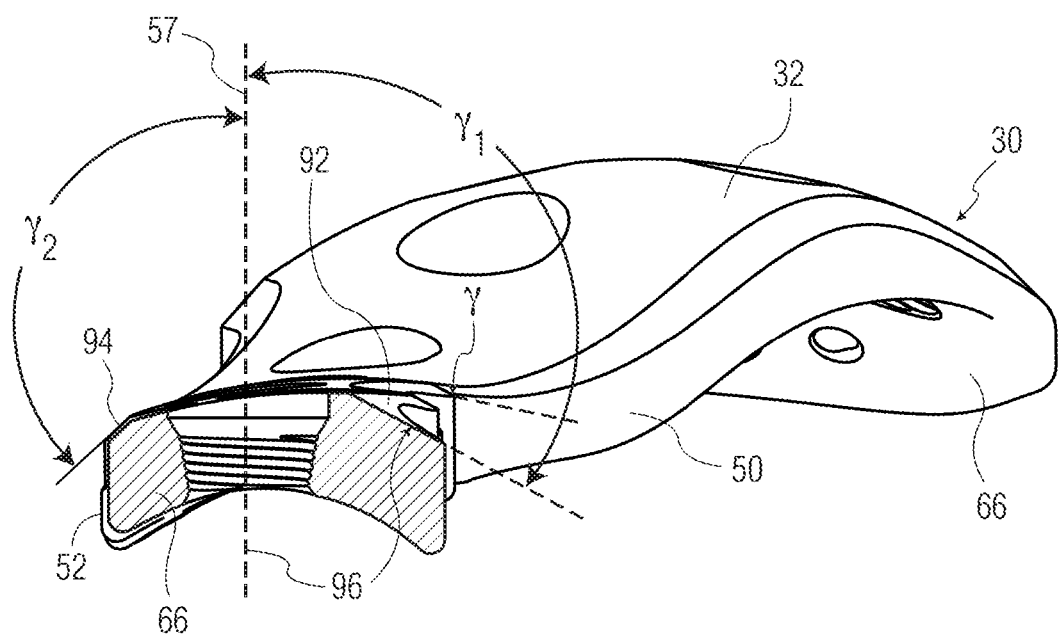

Referring to FIG. 7, there is shown a cross-section along lines 7-7 of FIG. 3 through the center 96 of hole 48, which now shows an enlarged chamfered area 60 of FIG. 2 shown as line 92 in FIG. 7 on side 50 of bone plate 30 with the shorter tapered or chamfered area 94 on side 52 of the plate 30. As can been seen in FIG. 2, the center 96 of hole 48 is located closer to side 52 than to side 50 of the bone plate. Chamfered area 60 extends to tip 62 to make insertion of the plate easier. Area 60 is angled at about 15° with respect to surface 32 at tip 62. Line 92 extends at angle γ2 towards surface 66 from line 57 and line 94 extends at γ2 from line 57.

Figure 8:
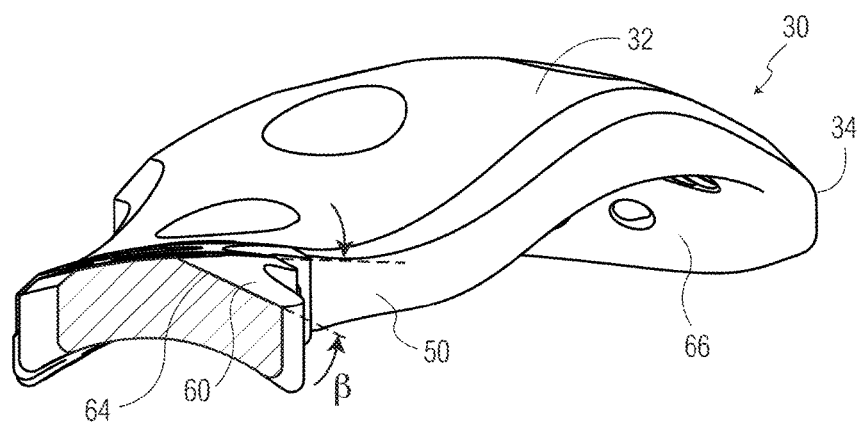

Referring to FIG. 8, there is shown a cross-section through lines 8-8 of FIG. 3 adjacent tip 62 showing chamfered area 60 extending towards side 50 of the bone plate. Chamfered area 60 extends along line 64 of FIG. 8 and an angle β with respect to the upper surface 32 of bone plate 30.

Figure 9:
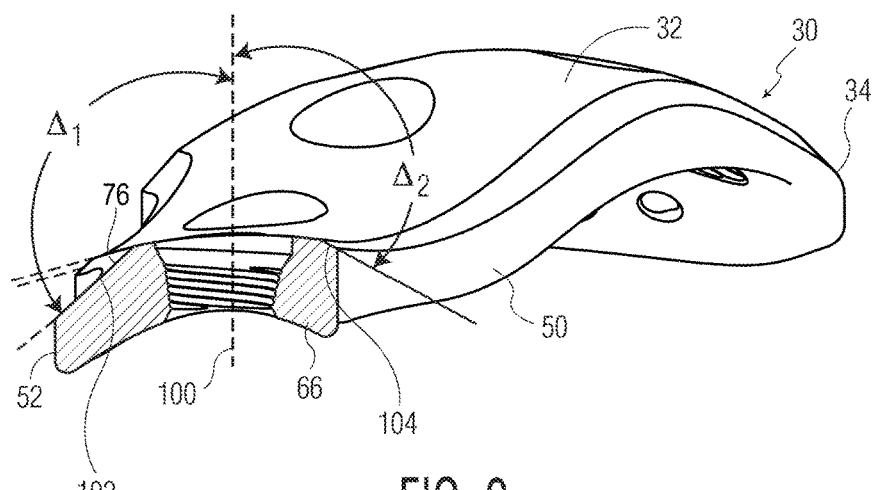

Referring to FIG. 9, there is shown a cross-section through the centerline of hole 42 of FIG. 3 in which the steeper, tapered or chamfered area 76 extends from upper surface 32 towards bone contacting surface 66 along side 52 defined by line 102 with a slope angle of Δ with taper 104 angled with respect to line 100 at Δ2. In this case, the line 100 through hole 42 is closer to side 50 of plate 30 than side 52. Such would be similar to hole 46 with regard to the cross-section shown in FIG. 5.

The use of alternating chamfered areas allowed by offsetting neighboring holes with respect to the centerline in opposite directions for the holes 42, 44, 46, and 48 allows for a more flexible bone plate, which is lighter than the prior art bone plates.

The fabrication method includes choosing a hole axis 51, 53, 55, or 57 to be the reference for the angle of the chamfer which hole axis may or may not be perpendicular to the plate surface. This axis is the main reference axis for other features on the plate as well. The hole axis lies three-dimensional in the room with only one 2D view shown. Thus, one single chamfering tool can perform the operation of creating the chamfer In order for this to happen, the part is directed in the direction of the reference axis. The chamfering tool which has a constant angle, will then follow the inner line of the final chamfer to create the feature. The advantage being, that this creates the chamfer without changing tools and changing the clamping of the part in the clamping machine. This could also potentially be done on a three-axis machine vs. a five-axis machine. The additional step of creating the "foot" of the plate is now unnecessary since it is cut with the chamfer. The insertion end of the plate is very shallow, such that one can push it underneath soft tissue easily. Prior to this method, the insertion end was an additional manufacturing step and which was fairly complicated.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone plate comprising:
   a shaft having a bone contacting surface and an opposite outwardly facing surface, the shaft having first and second side surfaces spaced from a centerline of the shaft and a top surface segment extending on the outwardly facing surface, the top surface segment being delineated by an edge and being surrounded by a peripheral tapered surface extending from the edge of the top surface segment to a corresponding one of the first and second side surfaces, the first and second side surfaces defining a width of the shaft;
   a plurality of holes extending from the outwardly facing surface to the bone contacting surface spaced along the shaft, each of the holes located intermediate the width of the shaft within the top surface segment, a first hole of the plurality of holes having a geometric center located closer to the first side of the shaft than the centerline, and a second hole of the plurality of holes having a geometric center located closer to the second side of the shaft than the centerline;
   the peripheral tapered surface of the shaft having a first enlarged chamfered area extending from the top surface segment adjacent the first hole towards the second side surface of the shaft, a first smaller chamfered area extending from the top surface segment adjacent the first hole towards the first side surface of the shaft, a second enlarged chamfered area extending from the top surface segment adjacent the second hole to the first side surface of the shaft and a second smaller chamfered area extending from the top surface segment adjacent the second hole to the second side surface of the shaft.

2. The bone plate as set forth in claim 1, wherein the plurality of holes includes at least three circular holes with the first hole and a third hole closer to the first side of the plate and the second hole closer to the second side of the plate, the second hole located intermediate the first and third holes.

3. The bone plate as set forth in claim 1, wherein the shaft centerline is curved.

4. The bone plate as set forth in claim 3, wherein the first and second side surfaces are scalloped with portions extending toward and away from the centerline along a length of the bone plate shaft.

5. The bone plate as set forth in claim 1, wherein the bone contacting surface between the first and second side surfaces is concave.

6. The bone plate as set forth in claim 1, wherein the peripheral tapered surface is spaced from the bone contacting surface by a portion of the corresponding one of the first or second side surfaces.

7. The bone plate as set forth in claim 1, wherein the shaft has a free end,
wherein the first and second side surfaces converge to form a tip with a width tapering inwardly towards the centerline, the tip has a rounded end and with a third hole of the plurality of holes adjacent the tip, the third hole offset from the centerline towards the first wall, the first and second side surfaces tapering outwardly from the top surface segment around the third hole to the bone contacting surface around a circumference of the tip rounded end, a taper angle of the second side surface from the top surface segment around the third hole to the bone contacting surface being less than a taper angle from the top surface segment to the bone contacting surface of the first side surface.

8. The bone plate as set forth in claim 2, wherein the plurality of holes includes five circular holes with the first, the third and a fifth holes located closer to the first side of the shaft from the centerline and the second and a fourth holes located closer to the second side of the shaft from the centerline.

9. The bone plate as set forth in claim 1, wherein the holes are circular.

10. The bone plate as set forth in claim 1, wherein the first and second side surfaces are scalloped with portions extending toward and away from the centerline along a length of the bone plate shaft.

11. A bone plate comprising:
a head portion connected to a shaft portion, the head portion and the shaft portion having a bone contacting surface and an opposite outwardly facing surface, the shaft having first and second side surfaces spaced from a centerline of the shaft and a top surface segment extending on the outwardly facing surface, the top surface segment being delineated by an edge and being surrounded by a peripheral tapered surface extending from the edge of the top surface segment to a corresponding one of the first and second side surfaces, and the head portion, the first and second side surfaces defining a width of the shaft;
at least three holes extending from the outwardly facing surface, within the top surface segment, to the bone contacting surface spaced along the shaft portion, each of the holes located intermediate the width of the shaft, each of a first and a third hole of the at least three holes having a geometric center located closer to the first side of the shaft than the centerline of the shaft, and a second hole of the at least three holes having a geometric center located closer to the second side of the shaft than the centerline;
the peripheral tapered surface of the shaft having a first enlarged chamfered area extending from the top surface segment adjacent the first hole towards the second side surface of the shaft, a first smaller chamfered area extending from the top surface segment adjacent the first hole towards the first side surface of the shaft, a second enlarged chamfered area extending from the top surface segment adjacent the second hole to the first side surface of the shaft, and a second smaller chamfered area extending from the top surface segment adjacent the second hole to the second side surface of the shaft.

12. The bone plate as set forth in claim 11, wherein the first and third holes are closer to the first side surface of the plate and the second hole is closer to the second side surface of the plate, the second hole located intermediate the first and third holes.

13. The bone plate as set forth in claim 11, wherein the shaft centerline is curved.

14. The bone plate as set forth in claim 13, wherein the first and second side surfaces are scalloped with portions extending toward and away from the centerline along a length of the bone plate shaft.

* * * * *